United States Patent [19]

Sedun et al.

[11] Patent Number: 5,919,733
[45] Date of Patent: Jul. 6, 1999

[54] NON-STAINING HERBICIDAL SOAP

[75] Inventors: Frederick S. Sedun, Saanichton; Cameron D. Wilson, Victoria, both of Canada

[73] Assignee: W. Neudorff GmbH KG, Germany

[21] Appl. No.: 08/833,374

[22] Filed: Apr. 4, 1997

[51] Int. Cl.$^6$ ................................................. A01N 37/00
[52] U.S. Cl. .................................................. 504/320
[58] Field of Search .............................................. 504/320

[56] References Cited

U.S. PATENT DOCUMENTS

| | | | |
|---|---|---|---|
| 4,774,234 | 9/1988 | Puritch et al. | 514/86 |
| 4,975,110 | 12/1990 | Puritch et al. | 71/113 |
| 5,035,741 | 7/1991 | Puritch et al. | 71/113 |
| 5,093,124 | 3/1992 | Kulenkamphff | 424/406 |
| 5,098,467 | 3/1992 | Puritch et al. | 71/113 |
| 5,098,468 | 3/1992 | Puritch et al. | 71/113 |
| 5,106,410 | 4/1992 | Puritch et al. | 71/113 |

FOREIGN PATENT DOCUMENTS

| | | | |
|---|---|---|---|
| 2247621 | 9/1990 | United Kingdom | A01N 31/02 |

OTHER PUBLICATIONS

Shepard, H.H, *The Chemistry and Toxicology of Insecticides,* Burgess Publication Co., Minneapolis (1947), pp. 227–230.

Savage et al., (CA 125:295228, WO 9628022).

Savage et al., CA 122:74589, US Patent 5366995.

Savage et al., CA 118:54335, WO 9219104.

*Primary Examiner*—Jose' G. Dees
*Assistant Examiner*—Sabiha N. Qazi
*Attorney, Agent, or Firm*—Nutter, McClennen & Fish, LLP

[57] ABSTRACT

An effective, environmentally compatible herbicidal composition utilizes under saponified ammonium soaps of fatty acids having from 6 to 11 carbon atoms. Potassium and sodium soap compositions, at 90 to 100% saponification, are effective to kill mosses, lichen, liverworts and algae, without damage to higher plants. The compositions are herbicidally effective and do not stain substrates, such as patios, walks, stairs, walls and the like, to which it is applied.

10 Claims, No Drawings

NON-STAINING HERBICIDAL SOAP

CROSS REFERENCE TO RELATED APPLICATIONS

Not applicable.

STATEMENT REGARDING FEDERALLY SPONSORED RESEARCH

Not applicable.

BACKGROUND OF THE INVENTION

The invention relates to herbicidally effective compositions, and particularly to those that include naturally occurring active ingredients.

Many herbicides are known and used in agricultural, commercial and household applications to control and/or eliminate a variety of unwanted weeds and other plants. Historically, the most effective and widely used herbicides are petrochemical-based products. Although effective herbicides, these compounds have come under close scrutiny because some can be harmful to humans and other animals.

Herbicides and other pesticides have more recently been formulated from naturally occurring active ingredients such as fatty acids or fatty acid salts. Some herbicides use fatty acids and fatty acid salts as co-active ingredients with other compounds. Examples of such compositions are disclosed in British Patent No. 2,247,621 and U.S. Pat. Nos. 4,774,234; 4,975,110; 5,035,741; and 5,106,410.

Herbicides are commonly applied to driveways, sidewalks, patios, walls, and similar structures to eliminate any weeds or mosses growing in joints or cracks in such structures. Certain known fatty acid and fatty acid salt herbicides can leave behind an unsightly white residue when applied to these substrates. Such known herbicides, although chemically effective, have been a major source of customer complaint because they leave behind an aesthetically unpleasing residue.

There is thus a need for herbicidal compositions that are effective to control weeds, without leaving behind unsightly residue on substrates to which the compositions are applied.

SUMMARY OF THE INVENTION

The invention provides a herbicidally effective composition that utilizes naturally occurring active ingredients. The active ingredients comprise, in a herbicidally effective amount, under saponified soaps of fatty acids such as sorbic acid, caprylic acid, pelargonic acid, capric acid, undecylenic acid and mixtures thereof. The ratio of soap to free acid in the active ingredient is in the range of 3:4 to 9:1. Preferably, the active ingredients are ammonium, sodium or potassium soaps of the desired acids.

The composition, in a ready-to-use formulation, includes about 1.0 to 10.0 percent by weight of the under saponified soap having a ratio of soap to free acid in the range of about 3:4 to 9:1.

The composition of the invention provides a herbicide that is effective against a broad range of algae, liverworts, mosses and higher plants. The composition is particularly well suited for application to hard substrates, such as walks, walls, stairs, patios, and the like, upon which unwanted weeds are actively growing. A particular advantage of the composition is that the herbicidally effective composition is formed from under saponified soaps of fatty acids, and it does not leave behind any permanent residue on the substrates to which it is applied. This provides an important advantage because many naturally occurring herbicidal compositions are not acceptable for use on such substrates due to the chemical damage and residue they leave behind.

DETAILED DESCRIPTION OF THE INVENTION

The invention provides a herbicidal composition that, although relying on under saponified soaps of fatty acids, does not cause residual staining to substrates to which it is applied. The composition uses as an active ingredient one or a mixture of under saponified soaps. The herbicidal composition may also include additional components to enhance processability and shelf-life, such as emulsifiers, antifoaming agents, gums and solvents. Such additional components are not believed to contribute any herbicidal activity to the composition.

The active ingredients for use as herbicides against higher plants preferably are under saponified soaps of fatty acids having from 6 to 11 carbon atoms. Preferred under saponified soaps are made from fatty acids including sorbic acid, caprylic acid, pelargonic acid, capric acid, undecylenic acid and mixtures thereof. These compounds are saponified with a base such as ammonium hydroxide, potassium hydroxide, sodium hydroxide, monethanolamine, diethanolamine and triethanolamine. Preferred active ingredients are under saponified ammonium or potassium soaps of sorbic, caprylic, pelargonic, capric, undecylenic acids and mixtures thereof. The ratio of soap to free fatty acid is preferably in the range of 3:4 to 9:1.

A ready-to-use formulation for use as a herbicide for higher plants, mosses, lichens, liverworts and algae includes under saponified fatty acid ingredients at a concentration in the range of about 1.0 to 10.0% by weight where the ratio of soap to fatty acid is in the range of about 3:4 to 9:1. A preferred composition has about 1.25 to 2.50% by weight of soap and 0.625 to 3.33% by weight free fatty acid. A preferred composition of ammonium pelargonate soap active ingredient has about 1.50 to 2.25% by weight ammonium pelargonate soap and about 0.75 to 3.0 free pelargonic acid. This composition also includes one or more antifoaming agents, gums and a solvent. An emulsifier may be included as well.

Suitable emulsifiers, which may be present at 0 to 5 percent by weight, include Aerosols® A-196 (available from American Cyanamid) and Tween® 81 and Tween® 85 (both available from ICI). Emulsifiers can be useful to improve stability and dilution.

Antifoaming agents may be present at 0 to 1 percent by weight. Exemplary antifoaming agents include Antifoam CM Concentrate and Antifoam 8810 FG Concentrate, both of which are available from Harcos Chemical. Although this additive is not necessary, it has been found to reduce the amount of foam generated during manufacture, dilution, and spraying.

A gum component may be present at 0 to 1 percent by weight to increase the viscosity of the formulation. The gum also increases the droplet size, when the formulation is sprayed through a nozzle. Larger droplets are less likely to drift to non-target plants or to nearby people or animals. Exemplary gums include Rhodopol 23 (Rhone Poulenc), VanGel B (R. T. Vanderbilt), and Kelzan S (Merck & Co.).

The formulation may optionally include solvents at a concentration range of 0 to 5 percent by weight. Exemplary solvents include alcohols, such as isopropyl alcohol, ethanol, propanol, butanol, methanol, propylene glycol, glycerol, and tetrahydrofurfuryl alcohol, and vegetable oils, such as canola oil. The solvents are believed to be useful to increase the antifoaming activity of any anti-foaming agent. The solvent may also contribute to improved storability of the formulation.

Examples of preferred, ready-to-use (RTU) formulations are set forth below in Table 1.

TABLE 1

Exemplary RTU Formulations

| Ingredient | Concentration (% by wt.) | |
|---|---|---|
| | Form. 1 | Form. 2 |
| Distilled water | 94.11 | 94.11 |
| Ammonium Pelargonate (47% saponified) | 3.68 | 3.68 |
| Antifoam 8810FG | 0.125 | 0.125 |
| Kelzan S | 0.080 | — |
| Isopropyl alcohol | 2.000 | — |
| Rhodopol 23 | — | 0.080 |
| Propanol | — | 2.000 |

The RTU formulations can be prepared as follows. Most of the water is poured into a container of an appropriate size, retaining approximately 5% of the total volume of water. The ammonium hydroxide (or base) is then added. Next the acid is added gradually, while stirring the formulation. Any antifoaming agent is then mixed with the remaining water and added to the main solution. The gum component can then be dispersed in any alcohol component and gradually added to the main solution while stirring vigorously. After stirring for about 15 minutes the solution can be dispensed into appropriate containers.

An exemplary concentrated formulation is illustrated in Table 2.

TABLE 2

Exemplary Concentrate

| Ingredient | % by wt. |
|---|---|
| Distilled water | 61.95 |
| Ammonium Pelargonate (47% saponified) | 36.80 |
| Antifoam 8810 FG | 1.25 |

The concentrate is prepared by adding all but about 5% of the water to a container of an appropriate size, followed by the addition of the base. The acid is then added gradually added while stirring the solution. The antifoam component is then mixed with the remaining water and added to the main solution. After stirring for about 15 minutes the solution can be dispensed to appropriate containers.

An exemplary ready-to-use formulation that is effective against mosses and algae is as follows.

Moss/Algae RTU (RTU #2)

| Distilled water | 98.0% by wt. |
|---|---|
| Potassium perlargonate (90% saponified) | 2.0% by wt. |

This exemplary RTU formulation can be prepared by dissolving potassium hydroxide in water and then adding pelargonic acid while stirring until the acid has completely reacted with the base to form a clear solution.

An exemplary concentrated formulation that is effective against mosses and algae is as follows.

Moss/Algae Concentrate

| Propylene Glycol | 50.0% by wt. |
|---|---|
| Potassium Perlargonate (90% saponified) | 50.0% by wt. |

This concentrated formulation can be prepared by first mixing the propylene glycol and potassium hydroxide. Pelargonic acid is then added while stirring. The acid is allowed to completely react with the base, forming a clear solution.

The compositions of the present invention are useful in that they can be made from only naturally occurring ingredients, e.g., fatty acid, ammonium hydroxide, and water. As a result, these formulations can be readily broken down in the soil without risk of any environmental damage.

The following examples further describe the invention.

EXAMPLE 1

This test compared concrete staining and grass phytotoxicity of a range of ammonium soap compositions with fatty acid emulsions. Every formulation contained 1% propanol and 1% of Aerosol A-196 (Cyanamid) emulsifier. The formulations were sprayed onto concrete and turf at a rate of 1.0 L/m$^2$. Commercially available fatty acid/salt based herbicides (TopGun (Safer, Ltd.), SpeedWeed (Pan Britannica Industries, Ltd.) and DeMoss (Safer, Ltd.)) were used as per their label recommendations. Every solution was sprayed onto 3 areas of grass and 2 areas of concrete. After drying overnight on concrete, the stains were washed with a garden hose and subjected to 5 days of natural rain before the "After Wash" concrete staining evaluation. The recorded rainfall on each of the five days between spraying and final evaluation was 2.2, 0.8, 2.6, 2.0, and 13.0 mm, respectively.

In each evaluation, a "0" to "9" rating scale was used to evaluate concrete staining, with "0" indicating no visible residue and "9" indicating severe white residue. Similarly, a "0" to "9" rating scale was used to evaluate plant phytotoxicity, with "0" indicating no plant damage and "9" indicating all of the sprayed plant surfaces were killed. The results are illustrated in Table 3.

TABLE 3

| Ammonium soap composition | | Concrete Staining (0 to 9) | | Grass Phytotoxicity |
|---|---|---|---|---|
| | (soap:acid) | Initial | After Wash | (0 to 9) |
| C8NH$_4$ soap | (1.12%:0.00%) | 0 | 0 | 3.5 |
| C8NH$_4$ soap | (0.56%:0.50%) | 0 | 0 | 7.0 |
| C8K soap | (1.26%:0.00%) | 0 | 0 | 1.8 |
| C8K soap | (0.63%:0.50%) | 0 | 0 | 7.4 |
| C8 acid | (0.00%:1.00%) | 0 | 0 | 8.9 |
| C9NH$_4$ soap | (1.11%:0.00%) | 0 | 0 | 3.8 |
| C9NH$_4$ soap | (0.55%:0.50%) | 0 | 0 | 7.3 |
| C9K soap | (1.24%:0.00%) | 3 | 0 | 1.4 |
| C9K soap | (0.62%:0.50%) | 5 | 0 | 8.5 |
| C9 acid | (0.00%:1.00%) | 3 | 0 | 9.0 |
| C10NH$_4$ soap | (1.10%:0.00%) | 2 | 0 | 5.3 |
| C10NH$_4$ soap | (0.55%:0.50%) | 3 | 0 | 7.2 |
| C10 acid | (0.00%:1.00%) | 7 | 0 | 8.7 |
| C10 K soap | (1.22%:0.00%) | 3 | 0 | 1.1 |
| C10 K soap | (0.61%:0.50%) | 8 | 0 | 8.5 |

TABLE 3-continued

| Ammonium soap composition | | Concrete Staining (0 to 9) | | Grass Phytotoxicity |
|---|---|---|---|---|
| | (soap:acid) | Initial | After Wash | (0 to 9) |
| C11:1NH₄ soap | (1.09%:0.00%) | 3 | 0 | 7.8 |
| C11:1NH₄ soap | (0.54%:0.50%) | 3 | 0 | 8.7 |
| C11:1 K soap | (1.21%:0.00%) | 4 | 0 | 1.8 |
| C11:1 K soap | (0.60%:0.50%) | 8 | 0 | 8.5 |
| C11:1 acid | (0.00%:1.00%) | 2 | 0 | 8.9 |
| C12NH₄ soap | (1.09%:0.00%) | 8 | 3 | 0.8 |
| C12NH₄ soap | (0.54%:0.50%) | 9 | 4 | 0.8 |
| C12 K soap | (1.21%:0.00%) | 4 | 0 | 1.8 |
| C12 K soap | (0.60%:0.50%) | 8 | 0 | 8.5 |
| C12 acid | (0.00%:1.00%) | 9 | 6 | 0.8 |
| Coconut NH₄ soap | (1.09%:0.00%) | 4 | 3 | 1.3 |
| Coconut NH₄ soap | (0.54%:0.50%) | 6 | 6 | 0.6 |
| Coconut K soap | (1.18%:0.00%) | 8 | 7 | 0.5 |
| Coconut K soap | (0.59%:0.50%) | 9 | 9 | 1.0 |
| Coconut acid | (0.00%:1.00%) | 9 | 9 | 3.4 |
| TopGun | | 2 | 1 | 8.6 |
| SpeedWeed | | 9 | 1 | 6.7 |
| DeMoss | | 8 | 8 | 0.7 |
| Base Formulation | | 0 | 0 | 0.1 |
| Water | | 0 | 0 | 0.0 |

EXAMPLE 2

The purpose of this test was to determine which ammonium soap compositions of various fatty acids stain concrete. Each solution contained the active ingredient noted below in specified amounts, as well as 3% isopropyl alcohol. The solutions were sprayed onto areas of an exposed concrete sidewalk at a rate of 0.5 L/m². After drying, the formulations were washed with a garden hose and evaluated. A final evaluation was made 3 weeks after spraying. The data are illustrated below in Table 4.

TABLE 4

| Ammonium Soap Composition | | Concrete Staining (0 to 9) | | |
|---|---|---|---|---|
| | (soap:acid) | Initial | After Wash | 3 Weeks |
| C8NH₄ soap | (3.35%:0.00%) | 0 | 0 | 0 |
| C8NH₄ soap | (2.68%:0.60%) | 0 | 0 | 0 |
| C8NH₄ soap | (2.01%:1.20%) | 0 | 0 | 0 |
| C8NH₄ soap | (1.34%:1.80%) | 0 | 0 | 0 |
| C8 K soap | (3.78%:0.00%) | 0 | 0 | 0 |
| C8 K soap | (3.02%:0.60%) | 0 | 0 | 0 |
| C8 K soap | (2.26%:1.20%) | 3 | 0 | 0 |
| C8 K soap | (1.51%:1.80%) | 4 | 0 | 0 |
| C9NH₄ soap | (3.32%:0.00%) | 0 | 0 | 0 |
| C9NH₄ soap | (2.65%:0.60%) | 0 | 0 | 0 |
| C9NH₄ soap | (1.99%:1.20%) | 0 | 0 | 0 |
| C9NH₄ soap | (1.33%:1.80%) | 0 | 0 | 0 |
| C9 K soap | (3.72%:0.00%) | 0 | 0 | 0 |
| C9 K soap | (2.98%:0.60%) | 6 | 0 | 0 |
| C9 K soap | (2.23%:1.20%) | 7 | 4 | 0 |
| C9 K soap | (1.49%:1.80%) | 9 | 4 | 0 |
| C10NH₄ soap | (3.30%:0.00%) | 0 | 0 | 0 |
| C10NH₄ soap | (2.64%:0.60%) | 0 | 0 | 0 |
| C10NH₄ soap | (1.98%:1.20%) | 0 | 0 | 0 |
| C10NH₄ soap | (1.32%:1.80%) | 0 | 0 | 0 |
| C10 K soap | (3.66%:0.00%) | 0 | 0 | 0 |
| C10 K soap | (2.93%:0.60%) | 0 | 0 | 0 |
| C10 K soap | (2.20%:1.20%) | 5 | 2 | 0 |
| C10 K soap | (1.47%:1.80%) | 9 | 6 | 3 |
| C11:1NH₄ soap | (3.26%:0.00%) | 0 | 0 | 0 |
| C11:1NH₄ soap | (2.61%:0.60%) | 0 | 0 | 0 |
| C11:1NH₄ soap | (1.95%:1.20%) | 0 | 0 | 0 |
| C11:1NH₄ soap | (1.30%:1.80%) | 0 | 0 | 0 |
| C11:1 K soap | (3.62%:0.00%) | 0 | 0 | 0 |

TABLE 4-continued

| Ammonium Soap Composition | | Concrete Staining (0 to 9) | | |
|---|---|---|---|---|
| | (soap:acid) | Initial | After Wash | 3 Weeks |
| C11:1 K soap | (2.89%:0.60%) | 0 | 0 | 0 |
| C11:1 K soap | (2.17%:1.20%) | 0 | 0 | 0 |
| C11:1 K soap | (1.45%:1.80%) | 7 | 2 | 0 |
| Coconut NH₄ soap | (3.24%:0.00%) | 5 | 5 | 3 |
| Coconut NH₄ soap | (2.59%:0.60%) | 9 | 7 | 7 |
| Coconut NH₄ soap | (1.94%:1.20%) | 6 | 5 | 8 |
| Coconut NH₄ soap | (1.30%:1.80%) | 9 | 8 | 8 |
| Coconut K soap | (3.54%:0.00%) | 6 | 3 | 3 |
| Coconut K soap | (2.83%:0.60%) | 4 | 4 | 3 |
| Coconut K soap | (2.12%:1.20%) | 9 | 8 | 8 |
| Coconut K soap | (1.41%:1.80%) | 9 | 9 | 9 |
| C9 soap RTU #2 | (1.82%:1.86%) | 0 | 0 | 0 |
| DeMoss | | 7 | 6 | 5 |
| Water | | 0 | 0 | 0 |

EXAMPLE 3

This test was conducted to study the concrete staining and grass phytotoxicity of several ammonium C9 soap (NH₄C9) compositions. All of the test solutions contained 4% isopropyl alcohol, 5% of Aerosol A-196 (Cyanamid) emulsifier. The solutions were sprayed onto concrete at a rate of 1.0 L/m², and allowed to dry. The treated concrete areas were evaluated the following morning. In the afternoon and evening, 28.6 mm of rain fell. The next morning another assessment was made of the treated concrete. The solutions were also sprayed onto 0.1 m² areas of established turf at a rate of 0.5 L/m². Turf phytotoxicity ratings were made 9 days after spraying. The data are illustrated below in Table 5.

TABLE 5

| C9 Ammonium Soap Composition | Concrete Staining (0 to 9) | | Turf Phytotoxicity |
|---|---|---|---|
| (soap:acid) | Before Rain | After Rain | (0 to 9) |
| (0.00%:4.00%) | 3 | 0 | 9 |
| (0.89%:3.20%) | 8 | 0 | 9 |
| (1.77%:2.40%) | 5 | 0 | 9 |
| (2.22%:2.00%) | 0 | 0 | 8 |
| (2.66%:1.60%) | 0 | 0 | 7 |
| (3.54%:0.80%) | 0 | 0 | 4 |
| (4.43%:0.00%) | 0 | 0 | 4 |
| Base Formulation | 0 | 0 | 0 |
| DeMoss | 8 | 8 | 0 |
| TopGun | 9 | 0 | 9 |
| Water | 0 | 0 | 0 |

EXAMPLE 4

The purpose of this test was to study the concrete staining of ammonium C11:1 soap compositions. Each formulation contained the active ingredient in the concentration identified below, as well as 3% isopropyl alcohol. The formulations were applied to a 0.1 m² area of concrete sidewalk at a rate of 50 ml per 0.1 m². TopGun and DeMoss were applied at their recommended rates of 7.26 g. product to 42.74 g. water, and 4.76 g. product to 95.24 g water, respectively. The data are illustrated in Tables 6A and 6B.

TABLE 6A

| C11:1 Ammonium soap composition (soap:acid) | White Stain After 1 Day (0 to 9) | White Stain After 1 Month (0 to 9) |
| --- | --- | --- |
| (3.26%:0.00%) | 0 | 0 |
| (2.61%:0.60%) | 0 | 0 |
| (1.95%:1.20%) | 0 | 0 |
| (1.63%:1.50%) | 0 | 0 |
| (1.30%:1.80%) | 2 | 0 |
| (0.98%:2.10%) | 5 | 0 |
| TopGun | 7 | 0 |
| DeMoss | 8 | 3 |
| Water | 0 | 0 |

TABLE 6B

| C11:1 K soap composition (soap:acid) | White Stain After 1 Day (0 to 9) | White Stain After 1 Month (0 to 9) |
| --- | --- | --- |
| (3.62%:0.00%) | 0 | 0 |
| (2.89%:0.60%) | 2 | 0 |
| (2.17%:1.20%) | 3 | 0 |
| (1.81%:1.50%) | 7 | 0 |
| (1.45%:1.80%) | 7 | 0 |
| (1.08%:2.10%) | 8 | 0 |
| C11:1 Na soap (1.68%:1.50%) | 5 | 0 |
| C9 soap RTU #2 (1.82%:1.86%) | 0 | 0 |

EXAMPLE 5

This test evaluated the concrete staining of SuperFast, TopGun, DeMoss, and an ammonium C11:1 soap composition containing 1.63% soap and 1.50% acid, 3.0% isopropyl alcohol and 0.25% CM Concentrate antifoam. DeMoss (40% soap) was diluted its recommended dilution of for moss on concrete of 4.76 g. product to 95.24 g. water. SuperFast (3% potassium soaps of fatty acids) was used without dilution. TopGun (18% fatty acids) was diluted to its recommended dilution of 7.26 g. product with 42.74 g. water. The formulations were each sprayed onto a 0.1 m² area of concrete sidewalk using a hand pump sprayer at a rate of 50 ml per 0.1 m². Two areas of concrete were used for every formulation. The amount of white residue was evaluated after 24 hours. After evaluation, the areas were thoroughly washed with water with a garden hose and re-evaluated after another 24 hours. A fmal evaluation was made 1 month after applying the formulations. The data are shown in Table 7.

TABLE 7

| | Concrete Staining (0 to 9) | | |
| --- | --- | --- | --- |
| Treatment | Before Wash | After Wash | 1 Month Weathering |
| Ammonium C11:1 soap composition | 0 | 0 | 0 |
| SuperFast | 8 | 5 | 0 |
| TopGun | 6 | 2 | 0 |
| DeMoss | 6 | 6 | 6 |
| Water | 0 | 0 | 0 |

The ammonium C11:1 soap composition did not stain concrete. The other formulations left a white residue after washing. After 1 month of normal weathering, the DeMoss-treated area still had a visible residue.

EXAMPLE 6

The purpose of this test was to compare the grass phytotoxicity and concrete staining of an ammonium C9 soap and potassium C9 soap compositions with the commercial products SpeedWeed, TopGun and DeMoss. The ammonium C9 composition contained 1.66% ammonium soap and 1.5% C9 acid, 3.0% isopropyl alcohol and 0.25% CM Concentrate antifoam. TopGun and DeMoss were applied at their recommended rates of 7.26 g. product to 42.74 g. water, and 4.76 g. product to 95.24 g. water, respectively. SpeedWeed was applied without dilution. The solutions were applied to concrete and turf at a rate of 0.25 L/m². Grass phytotoxicity was evaluated 2 days after spraying, concrete staining was evaluated after drying and again following a thorough washing. The data are shown in Table 8.

TABLE 8

| | Grass | Concrete Staining (0 to 9) | |
| --- | --- | --- | --- |
| Treatment | Phytotoxicity | Before Wash | After Wash |
| Ammonium C9 soap (1.66%:1.50%) | 7 | 0 | 0 |
| Potassium C9 soap (2.00%:0.00%) | 0 | 0 | 0 |
| SpeedWeed | 6 | 9 | 9 |
| TopGun | 5 | 8 | 5 |
| DeMoss | 0 | 8 | 8 |
| Water | 0 | 0 | 0 |

EXAMPLE 7

The purpose of this test was to compare the plant phytotoxicity and concrete staining of several commercially-available herbicides with an ammonium C9 soap composition and a potassium C9 soap composition. The ammonium C9 composition contained 1.66% ammonium soap, 1.5% C9 acid, 3.0% isopropyl alcohol and 0.25% CM Concentrate antifoam. The potassium C9 soap contained 2.0% potassium C9 soap, 0% C9 acid, 3% isopropyl alcohol and 0.25% CM Concentrate antifoam. The commercial fatty acid products were diluted as per their label directions.

The solutions were applied to concrete, weeds and turf at a rate of 0.20 L/m². The data displayed in Table 9 were collected at 1, 2, and 3 days after application for concrete staining and at 3 days for grass and weed phytotoxicity.

TABLE 9

| Evaluation | (before wash) | (after wash) | (after rain) |
| --- | --- | --- | --- |
| CONCRETE STAINING | 1 day | 2 days | 3 days |
| TopGun (diluted 1:7) | 8 | 6 | 1 |
| SpeedWeed RTU | 9 | 9 | 3 |
| SuperFast RTU | 9 | 9 | 3 |
| DeMoss (diluted 1:20) | 9 | 9 | 8 |
| Ammonium C9 soap composition | 0 | 0 | 0 |
| Potassium C9 soap composition | 0 | 0 | 0 |
| Water | 0 | 0 | 0 |
| GRASS PHYTOTOXICITY | 1 Day | 3 Days | |
| TopGun (diluted 1:7) | 8.9 | 8.8 | |
| SpeedWeed RTU | 8.9 | 8.9 | |
| SuperFast RTU | 8.9 | 8.9 | |
| Ammonium C9 soap composition | 8.8 | 8.8 | |

TABLE 9-continued

| Evaluation | (before wash) | (after wash) | (after rain) |
|---|---|---|---|
| DeMoss (diluted 1:32) | 0.0 | 0.0 | |
| Water | 0.0 | 0.0 | |
| CLOVER PHYTOTOXICITY *(Trifolium pretense)* | 3 hours | 1 day | 3 days |
| TopGun | 9.0 | 9.0 | 9.0 |
| Ammonium C9 soap composition | 8.0 | 8.5 | 8.5 |
| GROUNDSEL PHYTOTOXICITY *(Senico vulgaris)* | 3 hours | 1 day | 3 days |
| TopGun | 9.0 | 9.0 | 9.0 |
| Ammonium C9 soap composition | 7.0 | 9.0 | 9.0 |
| BROAD-LEAF PLANTAIN PHYTOTOXICITY *(Plantago major)* | 3 hours | 1 day | 3 days |
| TopGun | 9.0 | 9.0 | 9.0 |
| Ammonium C9 soap composition | 9.0 | 9.0 | 9.0 |
| FALSE DANDELION PHYTOTOXICITY *(Hyperchoerls redicata)* | 3 hours | 1 day | 3 days |
| TopGun | 1.0 | 9.0 | 9.0 |
| Ammonium C9 soap composition | 3.0 | 9.0 | 9.0 |

EXAMPLE 8

The purpose of this test was to compare the concrete staining of ammonium soaps of C6:2 (sorbate) and C9 (nonanoate) with DeMoss. The Sorbate formulations included the active ingredients in the concentrations noted below as well as 0.03% Silwet L-77 (Union Carbide Chemicals and Plastics Co.). The C9 ammonium soap RTU was that identified above as Formulation 1 in Table 1. The C9 ammonium soap concentrate was that identified above in Table 2. All of the solutions were applied to concrete at a rate of 1.0 L/m². Concrete staining was evaluated after drying overnight and after washing with water. The data are illustrated in Table 10.

TABLE 10

| | Concrete Staining (0 to 9) | |
|---|---|---|
| Composition | Before Wash | After Wash |
| C6:2 Ammonium Soap (2.02% soap:1.75% acid) | 0 | 0 |
| C6:2 Ammonium Soap (5.77% soap:5.00% acid) | 0 | 0 |
| C9 Ammonium Soap RTU (1.82% soap:1.86% acid) | 0 | 0 |
| C9 Ammonium Soap Concentrate (18.2% soap:18.6% acid) | 0 | 0 |
| DeMoss (Concentrate diluted 1:19) | 9 | 9 |

EXAMPLE 9

The purpose of this test was to compare the phytotoxicity of ammonium soaps of C6:2 (sorbate) and C9 (nonanoate) to nasturtium. The sorbate formulations included the active ingredients in the concentrations listed below, as well as 0.03% Silwet L-77. Each solution was sprayed onto four 3-week old nasturtiums until "run-off," and allowed to dry. The next day the amount of necrotic tissue (phytotoxicity) was assessed using a "0" to "9" scale, with a "9" indicating plant death. The data are shown in Table 11.

TABLE 11

| Formulation | Phytotoxicity (0 to 9) |
|---|---|
| C9 Ammonium Soap (0.98% soap:1.00% acid) | 8 |
| C6:2 Ammonium Soap (1.15% soap:1.00% acid) | 6 |
| Untreated | 0 |

EXAMPLE 10

The purpose of this test was to compare the concrete staining and grass phytotoxicity of completely saponified soaps, under saponified soaps, and acid solutions. The solutions of soaps and mixtures of soaps and acids were made using the indicated fatty acid, ammonium hydroxide and water. No other ingredients, such as alcohols or other solvents, were used.

For the solutions of acids, emulsified canola oil was used as a solvent. These formulations contained the fatty acid (2%), canola oil (4%), Tween 81 emulsifier (0.625%, ICI) and Tween 85 emulsifier (0.375%, ICI), and water (93 %). No other ingredients were used. A solution of canola oil, emulsifiers and water was included as a control.

Three other C9 fatty acid formulations were evaluated to compare the influence of gums and 2% isopropyl alcohol on concrete staining and grass phytotoxicity. Formulation C9-1 was the exemplary RTU formulation 1 noted in Table 1, sprayed without dilution (1.82% soap; 1.86% acid) and diluted to 0.99% soap; 1.01% acid. Formulation C9-2 was the exemplary concentrate formation noted in Table 2 and diluted to 1.82% soap; 1.86% acid and 0.99% soap; 1.01% acid. Formulation C9-3 was the exemplary concentrate formulation noted in Table 2 and diluted to (1.82% soap; 1.86% acid) and (0.99% soap; 1.01% acid), with 2% isopropyl alcohol included in the diluted solutions.

Topgun, Speed Weed and DeMoss were made as per label directions and included in the test as standards.

Areas of concrete were sprayed using these solutions, at a rate of 0.5 L/m². The concrete staining was assessed after drying. During the following 2 days, 18 mm of rain fell on the concrete. Following the rain, the concrete was allowed to dry and concrete staining was again assessed.

The test solutions were also sprayed onto turf at a rate of 1.0 L/m². Grass phytotoxicity was assessed 2 days after spraying, using a "0" to "9" scale.

The data are illustrated in Table 12.

TABLE 12

| Formulation NH$_4$ | | Concrete Staining (0 to 9) | | Turf |
|---|---|---|---|---|
| soap conc. | acid conc. | Before Rain | After Rain | Phytotoxicity (0 to 9) |
| C8 | 2.0% | 0.00% | 0 | 0 | 3 |
| C8 | 1.0 | 1.0 | 0 | 0 | 5 |
| C8 | 0.0 | 2.0 | 0 | 0 | 7 |
| C9 | 2.0 | 0.0 | 0 | 0 | 2 |
| C9 | 1.0 | 1.0 | 1 | 0 | 7 |
| C9 | 0.0 | 2.0 | 0 | 0 | 7 |
| C10 | 2.0 | 0.0 | 1 | 0 | 2 |
| C10 | 1.0 | 1.0 | 2 | 0 | 6 |
| C10 | 0.0 | 2.0 | 5 | 0 | 8 |

TABLE 12-continued

| Formulation NH₄ | | Concrete Staining (0 to 9) | | Turf |
|---|---|---|---|---|
| soap conc. | acid conc. | Before Rain | After Rain | Phytotoxicity (0 to 9) |
| C11 | 2.0 | 0.0 | 1 | 0 | 3 |
| C11 | 1.0 | 1.0 | 1 | 0 | 7 |
| C11 | 0.0 | 2.0 | 0 | 0 | 8 |
| C12 | 2.0 | 0.0 | 5 | 7 | 1 |
| C12 | 1.0 | 1.0 | 5 | 7 | 1 |
| C12 | 0.0 | 2.0 | 9 | 6 | 1 |
| Coconut | 2.0 | 0.0 | 6 | 8 | 3 |
| Coconut | 1.0 | 1.0 | 9 | 9 | 1 |
| Coconut | 0.0 | 2.0 | 9 | 6 | 1 |
| C9-1 | 0.99 | 1.01 | 0 | 0 | 7 |
| C9-2 | 0.99 | 1.01 | 0 | 0 | 6 |
| C9-3 | 0.99 | 1.01 | 0 | 0 | 6 |
| C9-1 | 1.82 | 1.86 | 0 | 0 | 9 |
| C9-2 | 1.82 | 1.86 | 0 | 0 | 9 |
| C9-3 | 1.82 | 1.86 | 0 | 0 | 9 |
| TopGun (2.62% acids) | | | 6 | 1 | 9 |
| SpeedWeed (2.4% acids) | | | 8 | 5 | 9 |
| DeMoss (2% soap) | | | 8 | 8 | 1 |
| Canola only | | | 0 | 0 | 0 |
| Water | | | 0 | 0 | 0 |

EXAMPLE 11

The purpose of this test was to compare the concrete staining and grass phytotoxicity of completely ammonium saponified soaps, under saponified ammonium soaps, and acid solutions of C9 fatty acid.

For the solutions of C9 fatty acid, emulsified canola oil was used as a solvent. The formulations contained C9 fatty acid (3.62% to 4.00%), ammonium hydroxide (0.0% to 2.94% of a 27% solution), canola oil (4%), Tween 81 (0.625%, ICI) and Tween 85 (0.375%, ICI), and water to 100%. No other ingredients were used. A solution of canola oil, emulsifiers and water was included as a control.

TopGun, Speed Weed and DeMoss were made as per label directions and included in the test as standards.

The procedure outlined in Example 10 was followed and the data are illustrated in Table 13.

TABLE 13

| Formulation | | (0 to 9) | | Turf |
|---|---|---|---|---|
| (soap conc.) | (acid conc.) | Before Rain | After Rain | Phytotoxicity (0 to 9) |
| C9 | 4.0% | 0.0% | 0 | 0 | 4 |
| C9 | 3.5 | 0.5 | 0 | 0 | 4 |
| C9 | 3.0 | 1.0 | 0 | 0 | 8 |
| C9 | 2.5 | 1.5 | 0 | 0 | 8 |
| C9 | 2.0 | 2.0 | 0 | 0 | 9 |
| C9 | 1.5 | 2.5 | 0 | 0 | 9 |
| C9 | 1.0 | 3.0 | 5 | 0 | 9 |
| C9 | 0.5 | 3.5 | 6 | 0 | 9 |
| C9 | 0.0 | 4.0 | 5 | 0 | 9 |
| TopGun | | | 6 | 0 | 8 |
| SpeedWeed | | | 5 | 0 | 7 |
| DeMoss | | | 5 | 6 | 0 |
| Canola only | | | 0 | 0 | 0 |
| Water | | | 0 | 0 | 0 |

EXAMPLE 12

The purpose of this test was to study the concrete staining and phytotoxicity of potassium pelargonate - pelargonic acid compositions. The solutions were made from potassium hydroxide, pelargonic acid and water. No other ingredients were used. The concrete was sprayed at 0.5 L/m² and the turf was sprayed at 1.0 1/m². After drying, the concrete received 0.2 mm of rain. Following the light rain, the concrete dried and was assessed. The concrete was then thoroughly washed with water from a garden hose.

The data are illustrated in Table 14.

TABLE 14

| Potassium Soap Compositions | | Concrete Staining (0 to 9) | | |
|---|---|---|---|---|
| (Saponification) | (soap:acid) | Initial Stain | Light Rain | After Wash |
| KC9 | (100%) | (2.00%:0.00%) | 0 | 0 | 0 |
| KC9 | (95%) | (1.90%:0.08%) | 0 | 0 | 0 |
| KC9 | (90%) | (1.80%:0.16%) | 0 | 0 | 0 |
| KC9 | (85%) | (1.70%:0.24%) | 3 | 0 | 0 |
| KC9 | (80%) | (1.60%:0.32%) | 5 | 0 | 0 |
| KC9 | (75%) | (1.50%:0.40%) | 6 | 0 | 0 |
| KC9 | (70%) | (1.40%:0.48%) | 6 | 1 | 0 |
| KC9 | (65%) | (1.30%:0.56%) | 6 | 3 | 0 |
| KC9 | (60%) | (1.20%:0.64%) | 7 | 7 | 0 |
| KC9 | (55%) | (1.10%:0.73%) | 7 | 7 | 0 |
| KC9 | (50%) | (1.00%:0.81%) | 7 | 7 | 0 |
| KC9 | (45%) | (0.90%:0.89%) | 7 | 7 | 0 |
| KC9 | (40%) | (0.80%:0.97%) | 7 | 4 | 0 |
| DeMoss 2% | soap | | 9 | 9 | 9 |
| Speed Weed | 8 | | 8 | 7 | 5 |
| Water | 0 | | 0 | 0 | 0 |

EXAMPLE 13

The purpose of this test was to compare the moss and turf phytotoxicity, and concrete staining of soap acid mixtures of KC8, KC9 and NH₄C9, with DeMoss. The moss was sprayed at 1.0L/m², and the grass sprayed at 0.1 L/m². Part B is a repeat of the test using some of the treatments of Part A.

The data are shown in Table 15.

TABLE 15

| Ammonium and Potassium Soap Compositions (soap:acid) | | Moss Phytotoxicity (0 to 9) | | Grass Phyto- toxicity (0 to 9) | Concrete Stain (0–9) | |
|---|---|---|---|---|---|---|
| | | 1 day | 2 days | | Before Wash | After Wash |
| Part A | | | | | | |
| KC8 soap | (4.00%:0.00%) | 2 | 9 | 2 | | |
| KC9 soap | (4.00%:0.00%) | 5 | 9 | 2 | | |
| NH₄C9 | (1.82%:1.86%) | 8 | 9 | 8 | | |
| DeMoss | (4.00%:0.00%) | 5 | 9 | 0 | | |
| KC8 soap | (2.00%:0.00%) | 2 | 9 | 0 | 0 | 0 |
| KC9 soap | (2.00%:0.00%) | 8 | 9 | 0 | 0 | 0 |
| NH₄C9 | (0.91%:0.93%) | 9 | 9 | 8 | 0 | 0 |
| DeMoss | (2.00%:0.00%) | 7 | 9 | 1 | 6 | 6 |
| Water | | 0 | 0 | 0 | 0 | 0 |
| Part B | | | | | | |
| KC8 soap | (2.00%:0.00%) | 5 | 7 | | 1 | 0 |
| KC9 soap | (2.00%:0.00%) | 7 | 9 | | 1 | 0 |
| NH₄C9 | (0.91%:0.93%) | 9 | 9 | | 1 | 0 |
| DeMoss | (2.00%:0.00%) | 6 | 8 | | 7 | 6 |
| Water | | 0 | 0 | | 0 | 0 |

EXAMPLE 14

The purpose of this test was to compare the moss and turf phytotoxicity, and concrete staining of KC9 soap (100% saponified) and DeMoss. The moss and grass was sprayed at 1.0 L/m². The data are illustrated in Table 16.

TABLE 16

|  | Moss Phytotoxicity (0 to 9) | | | Concrete Stain (0–9) | |
| --- | --- | --- | --- | --- | --- |
|  | 1 day | 2 days | 14 days | Before Wash | After Wash |
| KC9 (1.25% soap) | 3 | 5 | 9 | 0 | 0 |
| DeMoss (1.25% soap) | 9 | 9 | 9 | 8 | 8 |
| Water | 0 | 0 | 0 | 0 | 0 |

EXAMPLE 15

The purpose of this test was to compare the moss and turf phytotoxicity, and concrete staining of KC9, NaC9, KC8 and NaC8 soaps (90% saponified) and DeMoss. The concrete was sprayed of 0.5 L/m2, and the moss and grass at 1.0 L/m2. With DeMoss, the recommended concentration for concrete is 2.00% soap, and for moss and grass is 1.25% soap.

TABLE 17

| Sodium and Potassium Soap Compositions (soap:acid) | Concrete Staining (0 to 9) | | Moss Phytotoxicity (0–9) | |
| --- | --- | --- | --- | --- |
|  | Initial Stain | After Wash | 2 Days | 5 Days |
| KC9 1.80%:0.20% | 2 | 0 |  |  |
| NaC9 1.80%:0.20% | 1 | 0 |  |  |
| KC8 1.80%:0.20% | 0 | 0 |  |  |
| NaC8 1.80%:0.20% | 0 | 0 |  |  |
| DeMoss 2.00%:0.00% | 9 | 9 |  |  |
| KC9 1.13%:0.12% |  |  | 8 | 9 |
| NaC9 1.13%:0.12% |  |  | 6 | 9 |
| KC8 1.13%:0.12% |  |  | 5 | 9 |
| NaC8 1.13%:0.12% |  |  | 5 | 9 |
| DeMoss 1.25%:0.00% |  |  | 2 | 9 |
| Water | 0 | 0 | 0 | 0 |

One of ordinary skill in the art will appreciate that modifications may be made to the compositions of the present invention without departing from its intended scope. All percentages recited herein are percentages by weight, unless otherwise noted. All references cited herein are expressly incorporated by reference in their entirety.

What is claimed is:

1. A herbicidal composition, consisting essentially of:
a herbicidally effective amount of an active ingredient selected from the group consisting of under saponified ammonium soaps of sorbic acid, caprylic acid, pelargonic acid, capric acid, undecylenic acid and mixtures thereof, wherein the active ingredient has a soap to free fatty acid ratio in the range of about 3:4 to 2:1,
the composition being herbicidally effective on a range of algae, liverworts, mosses and higher plants and exhibiting no residual staining of substrates to which it is applied.

2. The composition of claim 1 further comprising an emulsifier present at 0.1 to 5.0 percent by weight of the composition.

3. The composition of claim 2 further comprising an anti-foaming agent present at a concentration range of 0.1 to 1.0 percent by weight of the composition.

4. The composition of claim 3 further comprising a gum component present at 0.1 to 1.0 percent by weight of the composition.

5. The composition of claim 4 further comprising a solvent present at a concentration of 0.1 to 5.0 percent by weighting of the composition.

6. The composition of claim 1 wherein a ready-to-use formulation contains in the range of about 1.0 to 10.0 percent by weight of the under saponified soap.

7. The composition of claim 1 wherein the active ingredient is an ammonium soap of pelargonic acid having, in a ready-to-use formulation, approximately 1.25 to 2.50 percent by weight of a saponified active ingredient and approximately 0.625 to 3.33 percent by weight of a free fatty acid active ingredient.

8. A herbicidally active composition, consisting essentially of:
an active ingredient selected from the group consisting of under saponified ammonium soaps of sorbic acid, caprylic acid, pelargonic acid, capric acid, undecylenic acid and mixtures thereof, wherein the active ingredient has a soap to free fatty acid ratio in the range of about 3:4 to 2:1;
an emulsifier;
a gum component;
an antifoaming agent,
the composition being herbicidally effective on a range of algae, liverworts, mosses and higher plants and exhibiting no residual staining of substrates to which it is applied.

9. The composition of claim 5 wherein the active ingredient contains in a ready-to-use formulation, about 1.5 to 2.25 percent by weight of a saponified component and about 0.75 to 3.0 percent by weight of a free fatty acid.

10. A herbicidal composition, consisting essentially of
an emulsifier present at 0.1 to 5.0 percent by weight of the composition;
a gum component present at 0.1 to 1.0 percent by weight of the composition;
an antifoamning agent present at 0.1 to 1.0 percent by weight of the composition;
an emulsifier present at 0.1 to 5.0 percent by weight of the composition; and
a herbicidally effective amount of an under saponified active ingredient selected from the group consisting of ammonium sorbate, ammonium caprylate, ammonium pelargonate, ammonium caprate, ammonium undecylenate and mixtures thereof, wherein the active ingredient contains in the range of about 1.0 to 10.0 percent by weight of a saponified component and about 0.5 to 7.0 percent by weight of a free fatty acid, the composition exhibiting no residual staining of substrates to which it is applied.

* * * * *